United States Patent
Lee et al.

(10) Patent No.: US 10,518,089 B2
(45) Date of Patent: Dec. 31, 2019

(54) REVERSING RECRUITMENT ORDER BY ANODE INTENSIFICATION

(71) Applicant: Boston Scientific Neuromodulation Corporation, Valencia, CA (US)

(72) Inventors: Dongchul Lee, Agua Dulce, CA (US); Kerry Bradley, Glendale, CA (US); David K. L. Peterson, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 318 days.

(21) Appl. No.: 15/490,339

(22) Filed: Apr. 18, 2017

(65) Prior Publication Data
US 2017/0216598 A1 Aug. 3, 2017

Related U.S. Application Data

(63) Continuation of application No. 12/821,005, filed on Jun. 22, 2010, now abandoned.
(Continued)

(51) Int. Cl.
*A61N 1/36* (2006.01)
*A61N 1/375* (2006.01)
(Continued)

(52) U.S. Cl.
CPC ..... *A61N 1/36071* (2013.01); *A61N 1/36185* (2013.01); *A61N 1/375* (2013.01); *A61N 1/3787* (2013.01); *A61N 1/37241* (2013.01)

(58) Field of Classification Search
CPC ............. A61N 1/36074; A61N 1/3787; A61N 1/37241; A61N 1/36185; A61N 1/375
See application file for complete search history.

(56) References Cited

U.S. PATENT DOCUMENTS

| 6,516,227 B1 | 2/2003 | Meadows et al. |
| 6,675,046 B2 | 1/2004 | Holsheimer |
| (Continued) | | |

OTHER PUBLICATIONS

"U.S. Appl. No. 12/821,005, Advisory Action dated Jun. 18, 2014", 3 pgs.
(Continued)

*Primary Examiner* — Catherine M Voorhees
*Assistant Examiner* — Roland Dinga
(74) *Attorney, Agent, or Firm* — Schwegman Lundberg & Woessner, P.A.

(57) ABSTRACT

A method of providing therapy to a patient using a plurality of electrodes is provided. The electrodes are located adjacent a target neural tissue region having a first nerve fiber of a relatively small diameter and a second nerve fiber of a relatively large diameter. The method comprises sourcing electrical current from a local anode into the target neural tissue region. The method further comprises therapeutically sinking a first portion of the electrical current from the target neural tissue region into a local cathode. The method further comprises sinking a second portion of the electrical current into a cathode remote from the target neural tissue region. The ratio of the sourced electrical current over the first sunk electrical current portion has a value that allows the first nerve fiber to be recruited by the electrical current while preventing the second nerve fiber from being recruited by the electrical current.

20 Claims, 11 Drawing Sheets

Related U.S. Application Data (60) Provisional application No. 61/220,140, filed on Jun. 24, 2009.

(51) Int. Cl.
*A61N 1/372* (2006.01)
*A61N 1/378* (2006.01)

(56) References Cited

U.S. PATENT DOCUMENTS

| | | | |
|---|---|---|---|
| 6,850,802 | B2 | 2/2005 | Holsheimer |
| 6,895,280 | B2 | 5/2005 | Meadows et al. |
| 6,993,384 | B2 | 1/2006 | Bradley et al. |
| 7,444,184 | B2 | 10/2008 | Boveja et al. |
| 7,539,538 | B2 | 5/2009 | Parramon et al. |
| 8,355,798 | B2 | 1/2013 | Lee |
| 2003/0139781 | A1 | 7/2003 | Bradley et al. |
| 2004/0193231 | A1 | 9/2004 | David et al. |
| 2005/0267546 | A1 | 12/2005 | Parramon et al. |
| 2007/0142863 | A1 | 6/2007 | Bradley |
| 2008/0114416 | A1 | 5/2008 | Theriot et al. |
| 2008/0294211 | A1* | 11/2008 | Moffitt ............... A61N 1/0553 607/9 |
| 2009/0024189 | A1 | 1/2009 | Lee et al. |
| 2010/0121416 | A1 | 5/2010 | Lee |
| 2010/0331925 | A1 | 12/2010 | Peterson |
| 2010/0331926 | A1 | 12/2010 | Lee et al. |

OTHER PUBLICATIONS

"U.S. Appl. No. 12/821,005, Advisory Action dated Oct. 28, 2013", 3 pgs.
"U.S. Appl. No. 12/821,005, Appeal Brief filed Jul. 28, 2014", 14 pgs.
"U.S. Appl. No. 12/821,005, Appeal Brief filed Dec. 5, 2013", 13 pgs.
"U.S. Appl. No. 12/821,005, Appeal Decision dated Feb. 24, 2017", 9 pgs.
"U.S. Appl. No. 12/821,005, Examiner's Answer to Appeal Brief dated Oct. 23, 2014", 9 pgs.
"U.S. Appl. No. 12/821,005, Final Office Action dated Apr. 23, 2014", 10 pgs.
"U.S. Appl. No. 12/821,005, Final Office Action dated Aug. 16, 2013", 9 pgs.
"U.S. Appl. No. 12/821,005, Non Final Office Action dated Jan. 29, 2014", 9 pgs.
"U.S. Appl. No. 12/821,005, Non Final Office Action dated Feb. 20, 2013", 10 pgs.
"U.S. Appl. No. 12/821,005, Non Final Office Action dated Dec. 18, 2012", 10 pgs.
"U.S. Appl. No. 12/821,005, Reply Brief filed Nov. 23, 2014", 7 pgs.
"U.S. Appl. No. 12/821,005, Response filed Feb. 1, 2013 to Non Final Office Action dated Dec. 18, 2012", 9 pgs.
"U.S. Appl. No. 12/821,005, Response filed Mar. 9, 2014 to Non Final Office Action dated Jan. 29, 2014", 7 pgs.
"U.S. Appl. No. 12/821,005, Response filed May 20, 2013 to Non Final Office Action dated Feb. 20, 2013", 10 pgs.
"U.S. Appl. No. 12/821,005, Response filed Jun. 6, 2014 to Final Office Action dated Apr. 23, 2014", 8 pgs.
"U.S. Appl. No. 12/821,005, Response filed Oct. 15, 2013 to Final Office Action dated Aug. 16, 2013", 6 pgs.
Lee, Dongchul, et al., "System and Method for Increasing Relative Intensity Between Cathodes and Anodes of Neurostimulation System Using Pulse Slicing", U.S. Appl. No. 61/113,442,, (Nov. 11, 2008).
Lee, Dongchul, et al., "Use of Stimulation Pulse Shape to Control Neural Recruitment Order and Clinical Effect", U.S. Appl. No. 60/951,177,, (Jul. 20, 2007).
Peterson, David K. L, et al., "System and Method for Performing Percutaneous Nerve Field Stimulation with Concurrent Anode Intensified Spinal Cord Stimulation", U.S. Appl. No. 61/220,149, (Jun. 24, 2009).

* cited by examiner

REVERSING RECRUITMENT ORDER BY ANODE INTENSIFICATION

RELATED APPLICATION

The present application is a continuation of U.S. application Ser. No. 12/821,005, filed Jun. 22, 2010, which claims the benefit under 35 U.S.C. § 119 to U.S. provisional patent application Ser. No. 61/220,140, filed Jun. 24, 2009. The foregoing applications are hereby incorporated by reference into the present application in their entirety.

FIELD OF THE INVENTION

The present inventions relate to tissue stimulation systems, and more particularly, to systems and methods for adjusting the stimulation provided to tissue to optimize a therapeutic effect.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications, such as angina pectoris and incontinence. Deep Brain Stimulation (DBS) has also been applied therapeutically for well over a decade for the treatment of refractory Parkinson's Disease, and DBS has also recently been applied in additional areas, such as essential tremor and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems such as the Freehand system by NeuroControl (Cleveland, Ohio) have been applied to restore some functionality to paralyzed extremities in spinal cord injury patients.

Each of these implantable neurostimulation systems typically includes one or more electrode carrying stimulation leads, which are implanted at the desired stimulation site, and a neurostimulator implanted remotely from the stimulation site, but coupled either directly to the stimulation lead(s) or indirectly to the stimulation lead(s) via a lead extension. Thus, electrical pulses can be delivered from the neurostimulator to the stimulation electrode(s) to stimulate or activate a volume of tissue in accordance with a set of stimulation parameters and provide the desired efficacious therapy to the patient. A typical stimulation parameter set may include the electrodes that are sourcing (anodes) or returning (cathodes) the stimulation current at any given time, as well as the amplitude, duration, and rate of the stimulation pulses. The neurostimulation system may further comprise a handheld patient programmer to remotely instruct the neurostimulator to generate electrical stimulation pulses in accordance with selected stimulation parameters. The handheld programmer in the form of a remote control (RC) may, itself, be programmed by a clinician, for example, by using a clinician's programmer (CP), which typically includes a general purpose computer, such as a laptop, with a programming software package installed thereon.

When stimulating neural tissue, the order in which nerve fibers are electrically stimulated or activated (i.e., the neural recruitment order), which is governed by spatial and morphometric criteria, has been a known issue that can limit efficacy by resulting in side effects (e.g., dorsal root stimulation, motor fiber stimulation, non-root-related effects, such as temperature, proprioceptor, reflex arc nerves, etc) that preclude the programming of stimulation systems to recruit fibers that could have possibly increased efficacy of the therapy.

For example, the neural recruitment order may be correlated to the diameter of the nerve fibers that innervate the volume of tissue to be stimulated. In SCS, activation (i.e., recruitment) of large diameter sensory fibers is believed to reduce/block transmission of smaller diameter pain fibers via interneuronal interaction in the dorsal horn of the spinal cord. Activation of large sensory fibers also creates a sensation known as paresthesia that can be characterized as an alternative sensation that replaces the pain signals sensed by the patient.

Because larger nerve fibers have lower stimulation thresholds than smaller nerve fibers, the larger nerve fibers will normally be stimulated before smaller nerve fibers when located the same distance from the active electrode or electrodes. Because of this, dominant recruitment of large nerve fibers is often unavoidable, possibly leading to uncomfortable, intense sensations in unwanted areas, and in the case of SCS, preventing the recruitment of deeper and/or smaller nerve fibers that might increase the efficacy of the therapy.

Thus, a neurostimulation system that could reverse the recruit order with respect to nerve fiber size in a controllable manner would be valuable to "tune" the desired therapeutic effect of a neurostimulation application, such as SCS.

SUMMARY OF THE INVENTION

In accordance with the present inventions, a method of providing therapy to a patient using a plurality of electrodes located adjacent a target neural tissue region is provided. If the target neural tissue region comprises spinal cord tissue, the electrodes may, e.g., be rostro-caudally arranged along the spinal cord tissue. The target neural tissue region has a first nerve fiber of a relatively small diameter and a second nerve fiber of a relatively large diameter.

The method comprises sourcing electrical current (which may take the form of a series of electrical pulses) from two local anodes of the electrodes into the target neural tissue region, and therapeutically sinking a first portion of the electrical current from the target neural tissue region into at least one local cathode (which is flanked by the two local anodes) of the electrodes. The distance between the first nerve fiber and the geometric center of the local cathode(s) is equal to or greater than the distance between the second nerve fiber and the geometric center of the local cathode(s).

The method further comprises sinking a second portion of the electrical current into at least one cathode remote from the target neural tissue region. The first and second portions of the electrical current can be simultaneously distributed or temporally distributed between the local cathode(s) and remote cathode(s). In one method, the remote electrode(s) is disposed on a case of an implantable pulse generator. In another method, the remote electrode(s) is located adjacent another target neural tissue region, in which case, the second portion of the electrical current can be therapeutically sunk from the other target neural tissue region into the remote cathode(s). Significantly, the ratio of the sourced electrical current over the first sunk electrical current portion has a value that allows the first nerve fiber to be recruited by the electrical current while preventing the second nerve fiber from being recruited by the electrical current.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a spinal cord stimulation (SCS) system. However, it is to be understood that the while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
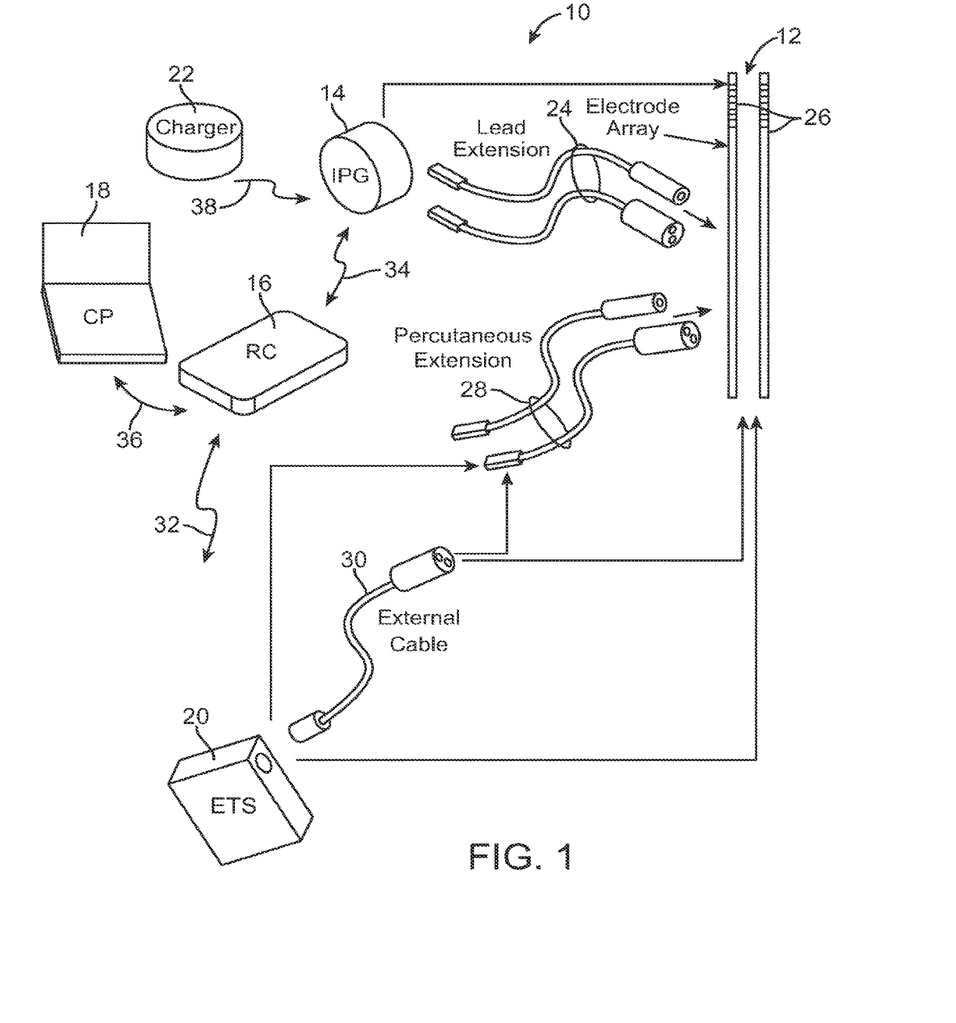
FIG. 1 is plan view of one embodiment of a spinal cord stimulation (SCS) system arranged in accordance with the present inventions.

Turning first to FIG. 1, an exemplary SCS system 10 generally includes one or more (in this case, two) implantable stimulation leads 12, an implantable pulse generator (IPG) 14, an external remote controller RC 16, a clinician's programmer (CP) 18, an External Trial Stimulator (ETS) 20, and an external charger 22.

The IPG 14 is physically connected via one or more percutaneous lead extensions 24 to the stimulation leads 12, which carry a plurality of electrodes 26 arranged in an array. In the illustrated embodiment, the stimulation leads 12 are percutaneous leads, and to this end, the electrodes 26 are arranged in-line along the stimulation leads 12. In alternative embodiments, the electrodes 26 may be arranged in a two-dimensional pattern on a single paddle lead. As will be described in further detail below, the IPG 14 includes pulse generation circuitry that delivers the electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the stimulation leads 12. The ETS 20, which has similar pulse generation circuitry as the IPG 14, also delivers electrical stimulation energy in the form of a pulse electrical waveform to the electrode array 26 accordance with a set of stimulation parameters. The major difference between the ETS 20 and the IPG 14 is that the ETS 20 is a non-implantable device that is used on a trial basis after the stimulation leads 12 have been implanted and prior to implantation of the IPG 14, to test the responsiveness of the stimulation that is to be provided.

The RC 16 may be used to telemetrically control the ETS 20 via a bi-directional RF communications link 32. Once the IPG 14 and stimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. The CP 18 provides clinician detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present.

For purposes of brevity, the details of the RC 16, CPS 18, ETS 20, and external charger 22 will not be described herein. Details of exemplary embodiments of these devices are disclosed in U.S. Pat. No. 6,895,280, which is expressly incorporated herein by reference.

Figure 2:
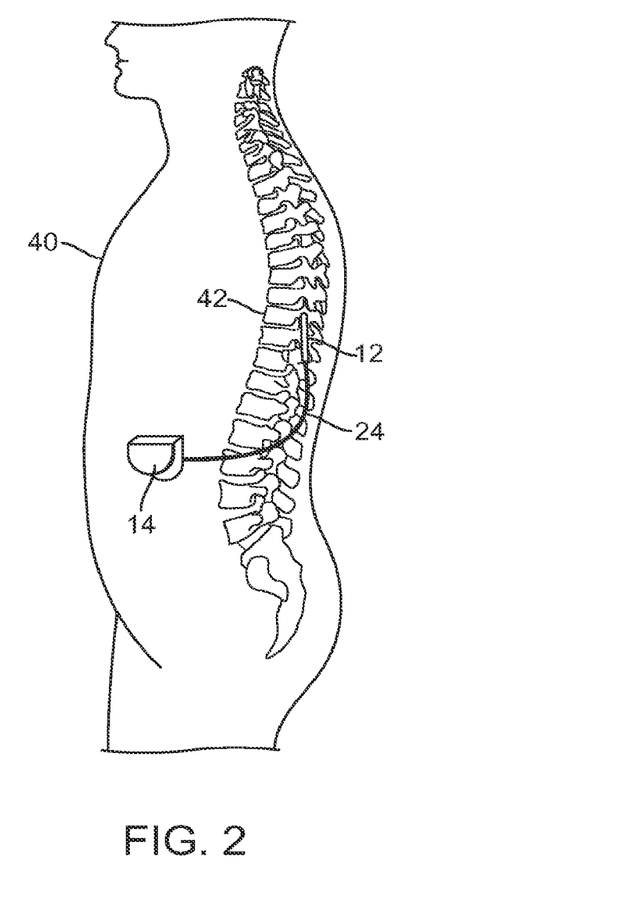
FIG. 2 is a plan view of the SCS system of FIG. 1 in use with a patient.

As shown in FIG. 2, the electrode lead 12 is implanted within the spinal column 42 of a patient 40. The preferred placement of the electrode lead 12 is adjacent, i.e., resting upon, the spinal cord area to be stimulated. Due to the lack of space near the location where the electrode leads 12 exit the spinal column 42, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the electrode leads 12. As there shown, the CP 18 communicates with the IPG 14 via the RC 16.

Figure 3:
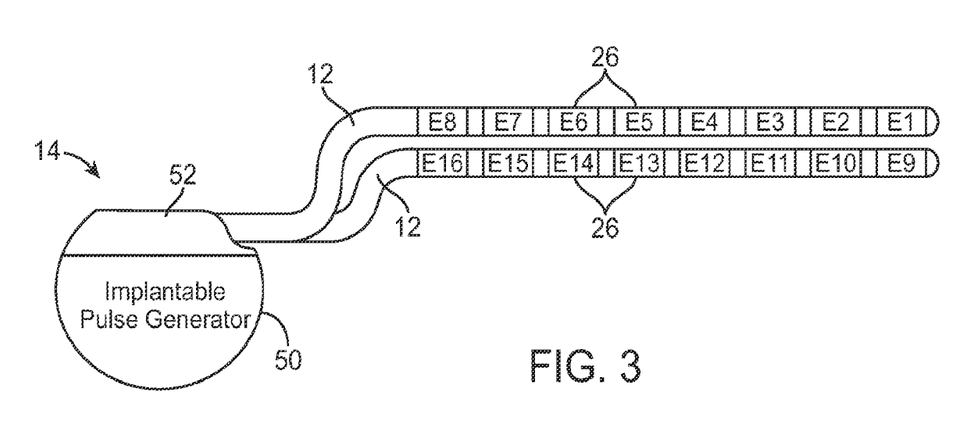
FIG. 3 is a plan view of an implantable pulse generator (IPG) and one embodiment of a stimulation lead used in the SCS system of FIG. 1.

Referring now to FIG. 3, the external features of the stimulation leads 12 and the IPG 14 will be briefly described. One of the stimulation leads 12 has eight electrodes 26 (labeled E1-E8), and the other stimulation lead 12 has eight electrodes 26 (labeled E9-E16). The actual number and shape of leads and electrodes will, of course, vary according to the intended application. The IPG 14 comprises an outer case 50 for housing the electronic and other components (described in further detail below), and a connector 52 to which the proximal ends of the stimulation leads 12 mate in a manner that electrically couples the electrodes 26 to the internal electronics (described in further detail below) within the outer case 50. The outer case 50 is composed of an electrically conductive, biocompatible material, such as titanium, and forms a hermetically sealed compartment wherein the internal electronics are protected from the body tissue and fluids. In some cases, the outer case 50 may serve as an electrode.

As briefly discussed above, the IPG 14 includes battery and pulse generation circuitry that delivers the electrical stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode current), and electrical pulse parameters, which define the pulse amplitude (measured in milliamps or volts depending on whether the IPG 14 supplies constant current or constant voltage to the electrode array 26), pulse width (measured in microseconds), and pulse rate (measured in pulses per second), pulse shape, and burst rate (measured as the stimulation on duration per unit time).

Electrical stimulation will occur between two (or more) activated electrodes, one of which may be the IPG case 50. Simulation energy may be transmitted to the tissue in a monopolar or multipolar (e.g., bipolar, tripolar, etc.) fashion. Monopolar stimulation occurs when a selected one of the lead electrodes 26 is activated along with the case 50 of the IPG 14, so that stimulation energy is transmitted between the selected electrode 26 and case 50. Bipolar stimulation occurs when two of the lead electrodes 26 are activated as anode and cathode, so that stimulation energy is transmitted between the selected electrodes 26. For example, electrode E3 on the first lead 12 may be activated as an anode at the same time that electrode E11 on the second lead 12 is activated as a cathode. Tripolar stimulation occurs when three of the lead electrodes 26 are activated, two as anodes and the remaining one as a cathode, or two as cathodes and the remaining one as an anode. For example, electrodes E4 and E5 on the first lead 12 may be activated as anodes at the same time that electrode E12 on the second lead 12 is activated as a cathode.

The stimulation energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) stimulation pulse and an anodic (positive) recharge pulse that is generated after the stimulation pulse to prevent direct current charge transfer through the tissue, thereby avoiding electrode degradation and cell trauma. That is, charge is conveyed through the electrode-tissue interface via current at an electrode during a stimulation period (the length of the stimulation pulse), and then pulled back off the electrode-tissue interface via an oppositely polarized current at the same electrode during a recharge period (the length of the recharge pulse).

Figure 4:
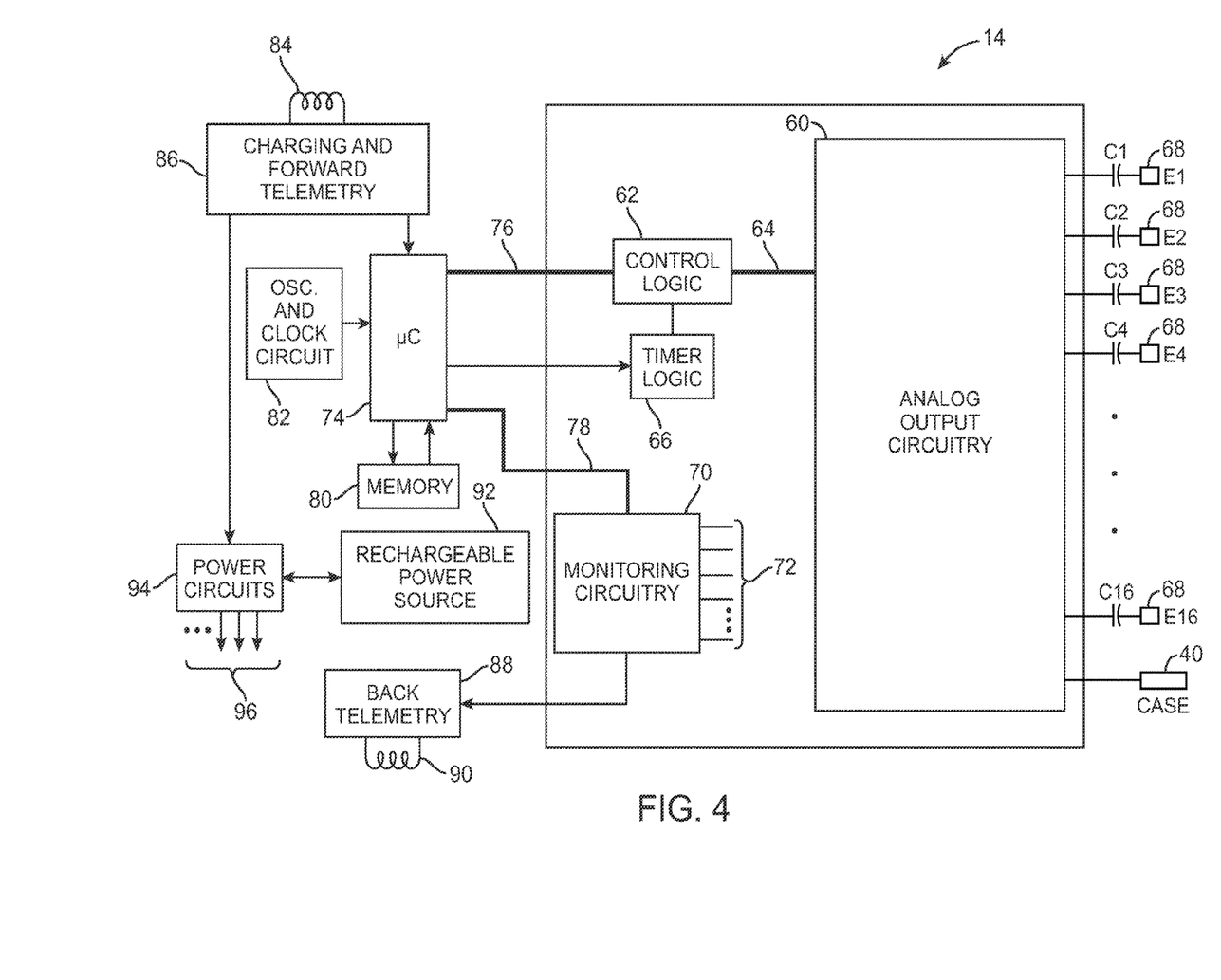
FIG. 4 is a block diagram of the internal components of the IPG of FIG. 3.

Turning next to FIG. 4, the main internal components of the IPG 14 will now be described. The IPG 14 includes stimulation output circuitry 60 configured for generating electrical stimulation energy in accordance with a defined pulsed waveform having a specified pulse amplitude, pulse rate, pulse width, pulse shape, and burst rate under control of control logic 62 over data bus 64. Control of the pulse rate and pulse width of the electrical waveform is facilitated by timer logic circuitry 66, which may have a suitable resolution, e.g., 10 μs. The stimulation energy generated by the stimulation output circuitry 60 is output via capacitors C1-C16 to electrical terminals 68 corresponding to the electrodes 26.

In the preferred embodiment, the analog output circuitry 60 comprises independently controlled current sources for providing stimulation pulses of a specified and known amperage to or from the electrical terminals 68, although in alternative embodiments, the analog output circuitry 60 may comprise independently controlled voltage sources for providing stimulation pulses of a specified and known voltage at the electrical terminals 68. The operation of this analog output circuitry, including alternative embodiments of suitable output circuitry for performing the same function of generating stimulation pulses of a prescribed amplitude and width, is described more fully in U.S. Pat. Nos. 6,516,227 and 6,993,384, which are expressly incorporated herein by reference. The analog output circuitry 60 may also comprise pulse shaping circuitry (not shown) capable of shaping the pulses (e.g., a square pulse, an exponential pulse, a logarithmic pulse, a ramped pulse, a trapezoidal pulse, etc.). Further details discussing pulse shaping circuitry and the different pulse shapes that can be generated are disclosed in U.S. Patent Application Ser. No. 60/951,177, entitled "Use of Stimulation Pulse Shape to Control Neural Recruitment Order and Clinical Effect," which is expressly incorporated herein by reference.

The IPG 14 further comprises monitoring circuitry 70 for monitoring the status of various nodes or other points 72 throughout the IPG 14, e.g., power supply voltages, temperature, battery voltage, and the like. The monitoring circuitry 70 is also configured for measuring electrical parameter data (e.g., electrode impedance and/or electrode field potential). The IPG 14 further comprises processing circuitry in the form of a microcontroller (μC) 74 that controls the control logic 62 over data bus 76, and obtains status data from the monitoring circuitry 70 via data bus 78. The IPG 14 further comprises memory 80 and oscillator and clock circuit 82 coupled to the microcontroller 74. The microcontroller 74, in combination with the memory 80 and oscillator and clock circuit 82, thus comprise a microprocessor system that carries out a program function in accordance with a suitable program stored in the memory 80. Alternatively, for some applications, the function provided by the microprocessor system may be carried out by a suitable state machine.

Thus, the microcontroller 74 generates the necessary control and status signals, which allow the microcontroller 74 to control the operation of the IPG 14 in accordance with a selected operating program and stimulation parameters. In controlling the operation of the IPG 14, the microcontroller 74 is able to individually generate stimulus pulses at the electrical terminals 68 using the analog output circuitry 60, in combination with the control logic 62 and timer logic circuitry 66, thereby allowing each electrical terminal 68 (and thus, each electrode 26) to be paired or grouped with other electrical terminals 68 (and thus, other electrodes 26), including the monopolar case electrode, to control the polarity, amplitude, rate, pulse width, pulse shape, burst rate, and channel through which the current stimulus pulses are provided. The microcontroller 74 facilitates the storage of electrical parameter data measured by the monitoring circuitry 70 within memory 80.

The IPG 14 further comprises a receiving coil 84 for receiving programming data (e.g., the operating program and/or stimulation parameters) from the external programmer (i.e., the RC 16 or CP 18) in an appropriate modulated carrier signal, and charging, and circuitry 86 for demodulating the carrier signal it receives through the receiving coil 84 to recover the programming data, which programming data is then stored within the memory 80, or within other memory elements (not shown) distributed throughout the IPG 14.

The IPG 14 further comprises back telemetry circuitry 88 and a transmission coil 90 for sending informational data to the external programmer. The back telemetry features of the IPG 14 also allow its status to be checked. For example, when the CP 18 initiates a programming session with the IPG 14, the capacity of the battery is telemetered, so that the CP 18 can calculate the estimated time to recharge. Any changes made to the current stimulus parameters are confirmed through back telemetry, thereby assuring that such changes have been correctly received and implemented within the implant system. Moreover, upon interrogation by the CP 18, all programmable settings stored within the IPG 14 may be uploaded to the CP 18.

The IPG 14 further comprises a rechargeable power source 92 and power circuits 94 for providing the operating power to the IPG 14. The rechargeable power source 92 may, e.g., comprise a lithium-ion or lithium-ion polymer battery or other form of rechargeable power. The rechargeable source 92 provides an unregulated voltage to the power circuits 94. The power circuits 94, in turn, generate the various voltages 96, some of which are regulated and some of which are not, as needed by the various circuits located within the IPG 14. The rechargeable power source 92 is recharged using rectified AC power (or DC power converted from AC power through other means, e.g., efficient AC-to-DC converter circuits, also known as "inverter circuits") received by the receiving coil 84.

To recharge the power source 92, the external charger 22 (shown in FIG. 1), which generates the AC magnetic field, is placed against, or otherwise adjacent, to the patient's skin over the implanted IPG 14. The AC magnetic field emitted by the external charger induces AC currents in the receiving coil 84. The charging and forward telemetry circuitry 86 rectifies the AC current to produce DC current, which is used to charge the power source 92. While the receiving coil 84 is described as being used for both wirelessly receiving communications (e.g., programming and control data) and charging energy from the external device, it should be appreciated that the receiving coil 84 can be arranged as a dedicated charging coil, while another coil, such as the coil 90, can be used for bi-directional telemetry.

Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference.

It should be noted that rather than an IPG, the SCS system 10 may alternatively utilize an implantable receiver-stimulator (not shown) connected to the stimulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Significant to the present inventions, the IPG 14 may be operated in a manner that increases the magnitude of electrical current at an anode or anodes local to a target stimulation site without increasing the magnitude of electrical current at a cathode or cathodes local to the target stimulation site. By increasing the intensity of the local anode(s) relative to that of the local cathode(s) (referred to herein as "anode-intensification"), the normal nerve fiber recruitment order (where large diameter nerve fibers are activated prior to small diameter nerve fibers) is reversed. That is, a relatively small diameter nerve fiber may be activated prior to a relatively large diameter nerve fiber, even though the respective nerve fibers are equi-distant from geometric center of the stimulating cathode(s). In this manner, the small diameter nerve fiber, which presumably contributes to the therapeutic effect, may be recruited without recruiting the large diameter nerve fibers, which presumably may otherwise contribute to a side effect under certain circumstances.

In the preferred embodiment, anode-intensification is achieved by sourcing the electrical current from at least one anode (in the example described below, two "guarding" anodes) into a target spinal cord tissue region, sinking a portion of the electrical current from the target spinal cord tissue region into at least one local cathode adjacent the target spinal cord tissue region (in the example described below, a single cathode), and sinking another portion of the electrical current from the target spinal cord tissue region into at least one cathode remote from the target spinal cord tissue region. In this manner, the ratio of the amount of electrical current sunk (the cathodic current) from the target spinal cord tissue region over the amount of electrical current sourced (the anodic current) into the target spinal cord tissue region will be greater than one. This anode-intensification ratio has a value that allows the first nerve fiber to be recruited by the electrical current while preventing the second nerve fiber from being recruited by the electrical current.

Figure 5:
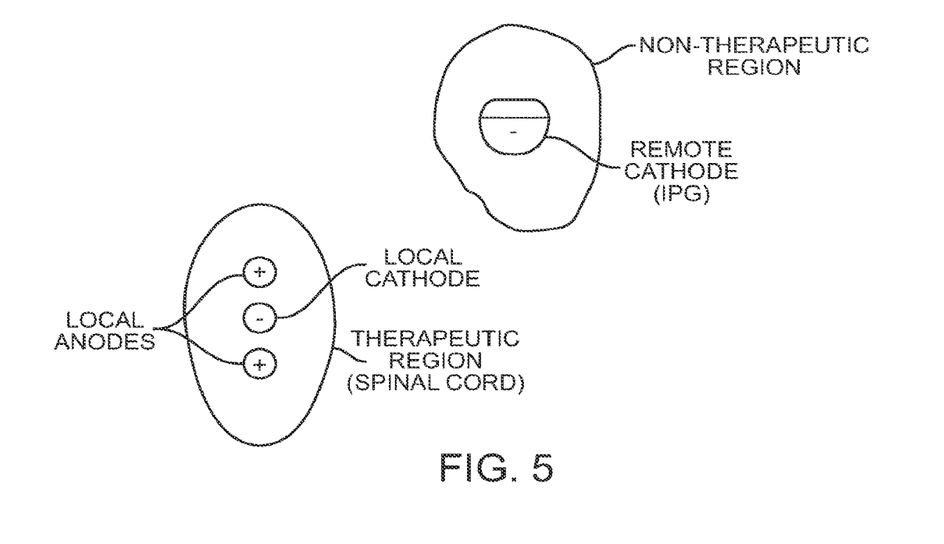
FIG. 5 is a plan view of one electrode arrangement used by the IPG of FIG. 3 to intensify anodes local to a target neural region.
Figure 6:
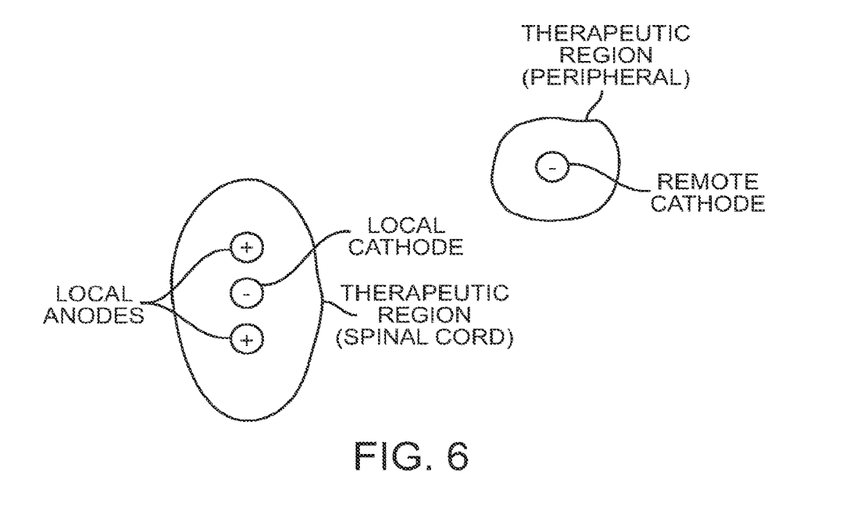
FIG. 6 is a plan view of another electrode arrangement used by the IPG of FIG. 3 to intensify anodes local to a target neural region.

As illustrated in FIG. 5, the remote cathode may be a non-therapeutic electrode (e.g., the IPG case 50 illustrated in FIG. 3) that is far enough from the target spinal cord tissue region to avoid significantly influencing the stimulation field at the local cathode, as described in U.S. Patent Publication No. 2007/0142863, which is expressly incorporated by reference. Alternatively, as illustrated in FIG. 6, the remote cathode may be a therapeutic electrode that is far enough from the target spinal cord tissue region (e.g., a remote cathode located in another therapeutic tissue region (e.g., a peripheral region) to avoid significantly influencing the stimulation field at the local cathode, as described in U.S. Patent Application Ser. No. 61/220,146, entitled "System and Method for Performing Percutaneous Nerve Field Stimulation with Concurrent Anode Intensified Spinal Cord Stimulation," which is expressly incorporated herein by reference.

Figure 7:
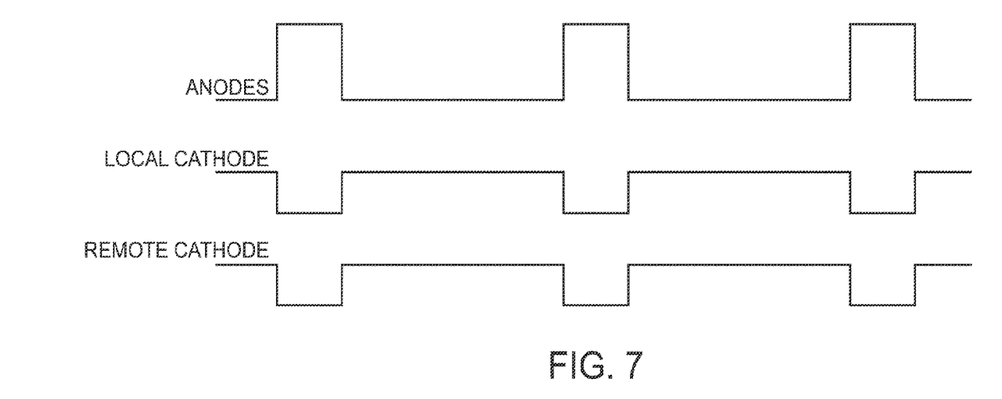
FIG. 7 is a timing diagram of one technique used by the IPG of FIG. 3 to intensify anodes using electrical pulses.

It should be noted that the portions of the cathodic electrical current can be simultaneously sunk from the target spinal cord tissue region (i.e., simultaneously distributed between the local cathode and remote cathode), as described in U.S. Patent Publication No. 2007/0142863, which has previously been incorporated by reference. For example, as shown in FIG. 7, for each anodic pulse that is generated with a given amplitude, two or more cathodic pulses (one local and the other or others remote) having a total amplitude of the anodic pulse amplitude can be simultaneously generated.

Figure 8:
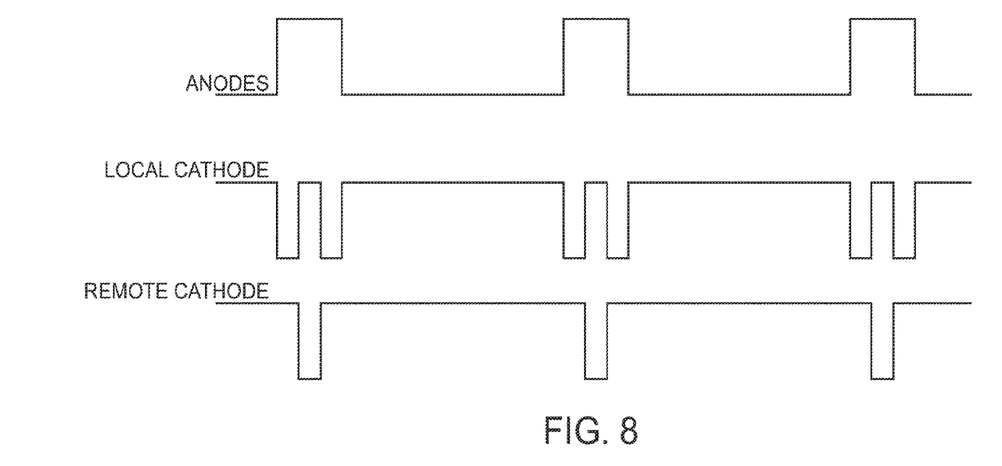
FIG. 8 is a timing diagram of another technique used by the IPG of FIG. 3 to intensify anodes using electrical pulses.

Alternatively, the portions of the cathodic electrical current can be temporally sunk from the target spinal cord tissue region (i.e., temporally distributed between the local cathode and the remote cathode), as described in U.S. Patent Application Ser. No. 61/113,442, entitled "System and Method for Increasing Relative Intensity Between Cathodes and Anodes of Neurostimulation System Using Pulse Slicing," which is expressly incorporated herein by reference. For example, as shown in FIG. 8, for each anodic pulse that is generated with a given amplitude and given pulse width, two or more cathodic pulses (one local and the other or others remote), each having the same amplitude as the anodic pulse amplitude, but having a pulse width shorter than the anodic pulse width, can be generated at different times during the anodic pulse. As shown in FIG. 8, for each anodic pulse delivered to the local anode, two cathodic pulses are delivered to the local cathode and a single cathodic pulse is delivered to the remote cathode. Due to the combined duration and close proximity of the cathodic pulses delivered to the local cathode, the target spinal cord tissue region will be stimulated by the local cathode. In contrast, the single cathodic pulse delivered to the remote cathode will not likely stimulate any tissue.

Figure 9:
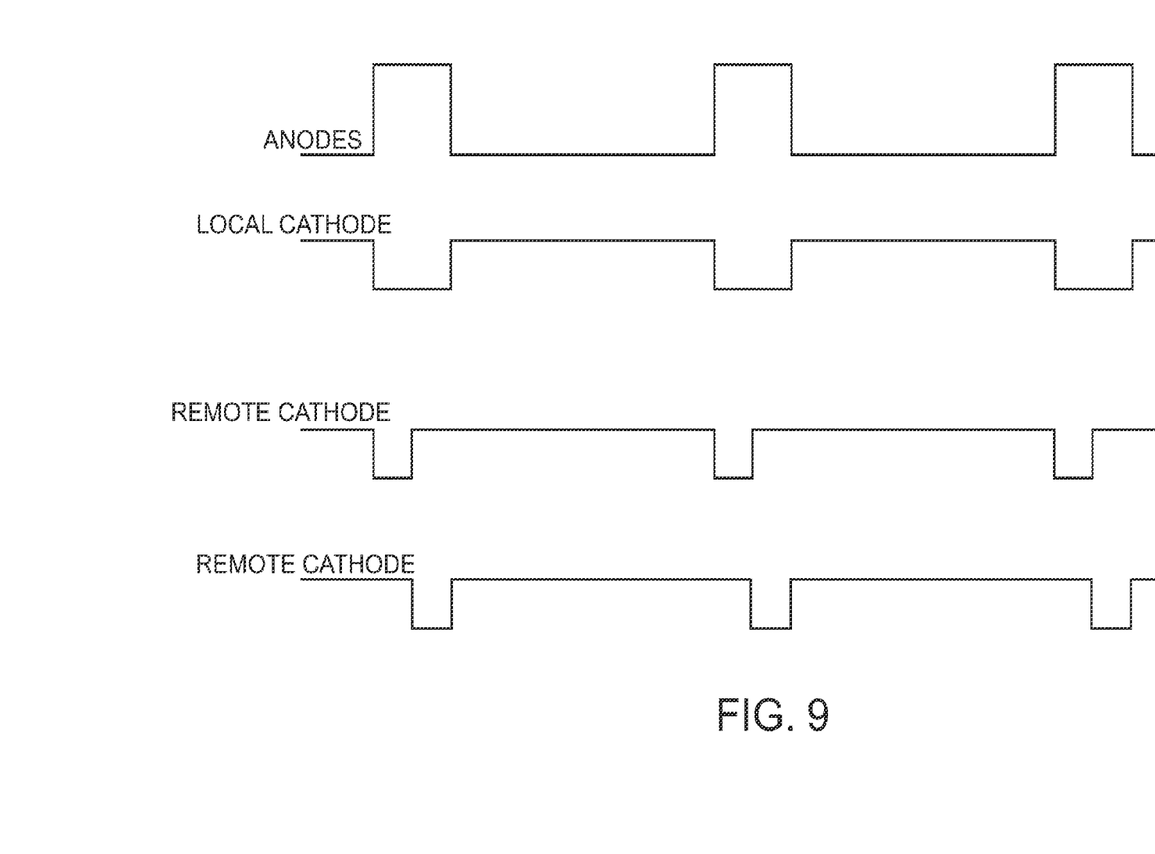
FIG. 9 is a timing diagram of still another technique used by the IPG of FIG. 3 to intensify anodes using electrical pulses.

Alternatively, only portions of the remote cathodic electrical current can be temporally sunk from the target spinal cord tissue region (i.e., temporally distributed between multiple remote cathodes). For example, as shown in FIG. 9, for each anodic pulse that is generated with a given amplitude and given pulse width, a cathodic pulse having the same pulse width, but smaller amplitude, is delivered to the local cathode, while cathodic pulses of smaller pulse widths and smaller amplitudes are temporally delivered to two remote cathodes to minimize the probability that nerve tissue is stimulated by the remote cathodes.

A conventional neural fiber modeling technique shows that "anode-intensification" reverses the typical "large-then-small" recruitment order in myelinated fibers. In particular, a tripolar rostro-caudal arrangement of electrodes, with a single cathode and two "guarding" anodes, as shown in FIGS. 5 and 6 was modeled for different sized nerve fibers (5.7 µm, 7.5 µm, 8.7 µm, 11.5 µm, 12.8 µm, and 14.0 µm), assuming a 4 mm center-to-center electrode distance, a spinal cord fluid depth (dCSF) of 2.0 mm, a perception threshold 1.4 times the dorsal root fiber stimulation threshold (1.4DRth), and a pulse width of 1 ms. The nerve fibers were assumed to be located on the surface of the dorsal column.

It was shown through this modeling that the recruitment penetration of relatively large-diameter nerve fibers using a rostro-caudal electrode arrangement with no anode intensification (i.e., the local cathodic current equals the local anodic current, such that the anode-intensification ratio is equal to 1) was deeper than the recruitment penetration of relatively small-diameter nerve fibers. However, when the anode-intensification ratio was increased to 2.4 (such that the local anode current from each flanking anode equals 120% of the local cathodic current through the flanked cathode, and the remainder of the cathodic current is sunk at the remote cathode), the recruitment penetration of relatively large-diameter nerve fibers was comparable to the recruitment penetration of relatively small-diameter nerve fibers. Because of the abundance of small nerve fibers in the dorsal column, the total number of recruited nerve fibers using anode intensification was approximately 2.5 times greater than the total number of recruited nerve fibers when no anode intensification is used.

Figure 10:
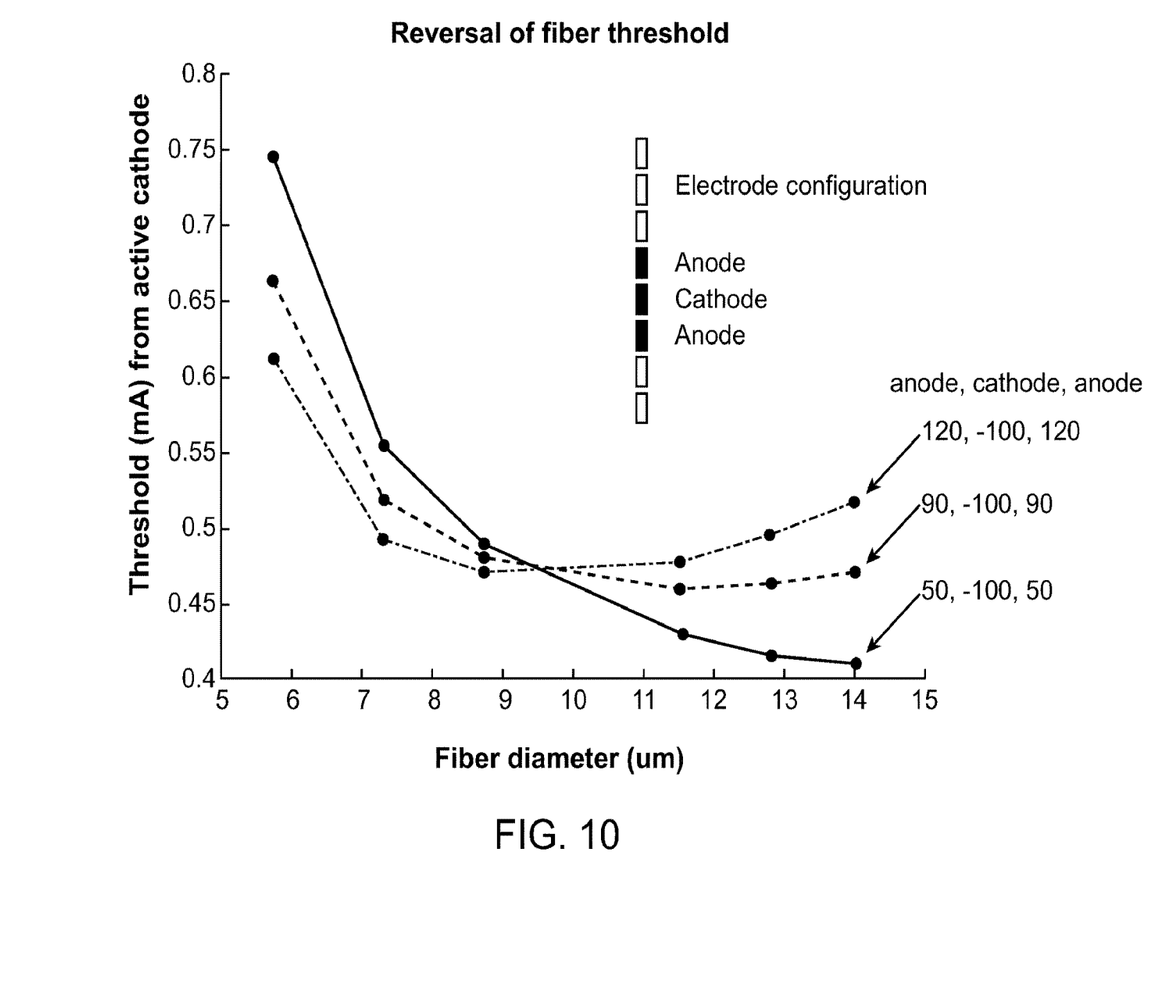
FIG. 10 is a plot showing the threshold of an active cathode plotted against the diameter of stimulated nerve fibers given a conventional current distribution on a tripolar electrode arrangement and two different anode intensification distributions on a tripolar electrode arrangement.

Referring to FIG. 10, the recruitment thresholds, measured in amperage of the current at the local cathode, were plotted versus the different nerve fiber diameters given different levels of anode intensification. As shown, under the normal conditions of locally balanced cathodic and anodic currents (i.e., no anode intensification, such that the anode-intensification ratio equals 1 (such that the local anode current from each flanking anode equals 50% of the local cathodic current sunk by the flanked cathode, and the remainder of the cathodic current is sunk at the remote cathode)), the recruitment order curve (solid line) is consistent with curves expected when using standard stimulation (monotonic decay as a function of nerve fiber diameter). When the anode-intensification ratio equals 1.8 (such that the local anode current from each flanking anode equals 90% of the local cathodic current sunk by the flanked cathode, and the remainder of the cathodic current is sunk at the remote cathode), the largest nerve fiber (14.0 µm) has a higher threshold than the 11.5 µm nerve fiber as dictated by the reverse recruitment order curve (dashed line) and when the anode-intensification ratio equals 2.4 (such that the local anode current from each flanking anode equals 120% of the local cathodic current sunk by the flanked cathode, and the remainder of the cathodic current is sunk at the remote cathode), the largest nerve fiber (14.0 µm) has a higher threshold than the 7.5 µm nerve fiber as dictated by the reverse recruitment order curve (dotted line), which is contrary to what is expected by conventional approaches. It should be noted that, although the flanking anodes are illustrated as having equal distributions, the anodes may have unequal current distributions in order to overcome tissue and distance effects that are more pronounced at one of the anodes, so that the distribution of current assures an equivalence of anodic hyperpolarization effects at the target neural tissue.

Referring to FIGS. 11A-11F, the mechanism the enables the reversing of the nerve fiber recruitment order will now be described. The tripolar electrode arrangement illustrated in FIG. 11A was modeled, assuming a 4 mm center-to-center electrode distance, a spinal cord fluid depth (dCSF) of 2.0 mm, a perception threshold of 99% of the nearby dorsal root fiber stimulation threshold (99DRth), and a pulse width of 1 ms. Two nerve fibers having a relatively large diameter of 14.0 μm, and a relatively small diameter of 7.3 μm, were modeled at a location within the dorsal column (shown by dot in FIG. 11B), where the small diameter nerve fiber would be recruited and the large diameter nerve fiber would not be recruited in accordance with the reverse recruitment order regimen.

Figure 11A:
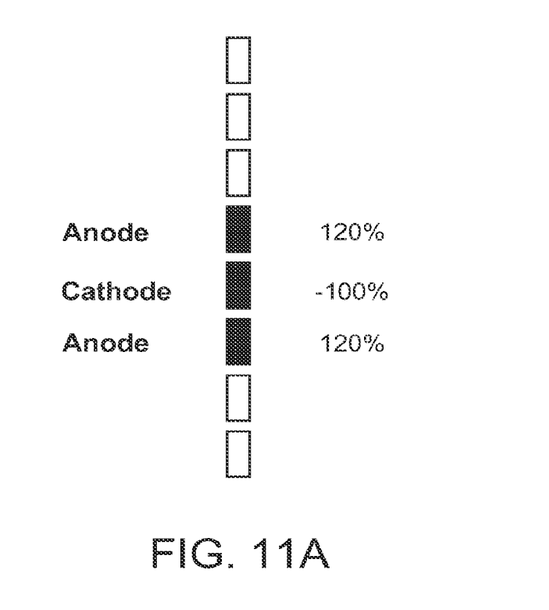
FIG. 11A is a plan view of a tripolar rostro-caudal electrode arrangement.
Figure 11B:
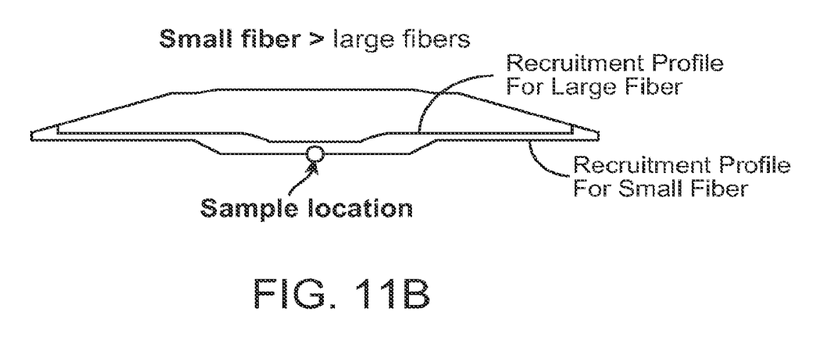
FIG. 11B is a plan view of modeled recruitment profiles for a large nerve fiber and a small nerve fiber that were modeled by intensifying the anodes in the tripolar rostro-caudal electrode arrangement of FIG. 11A.
Figure 11C:
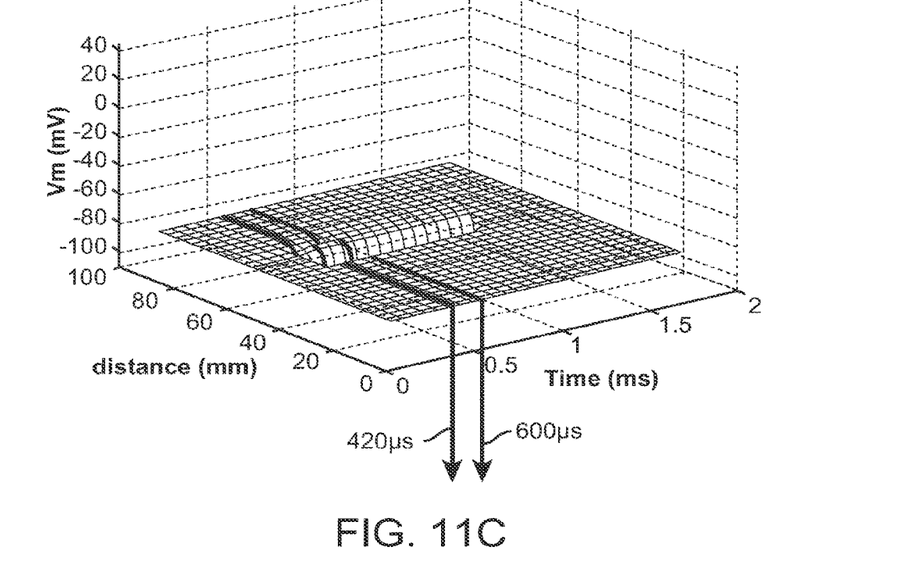
FIG. 11C is a three-dimensional diagram showing membrane voltage of the large diameter fiber of FIG. 11B plotted against time and distance along fiber.
Figure 11D:
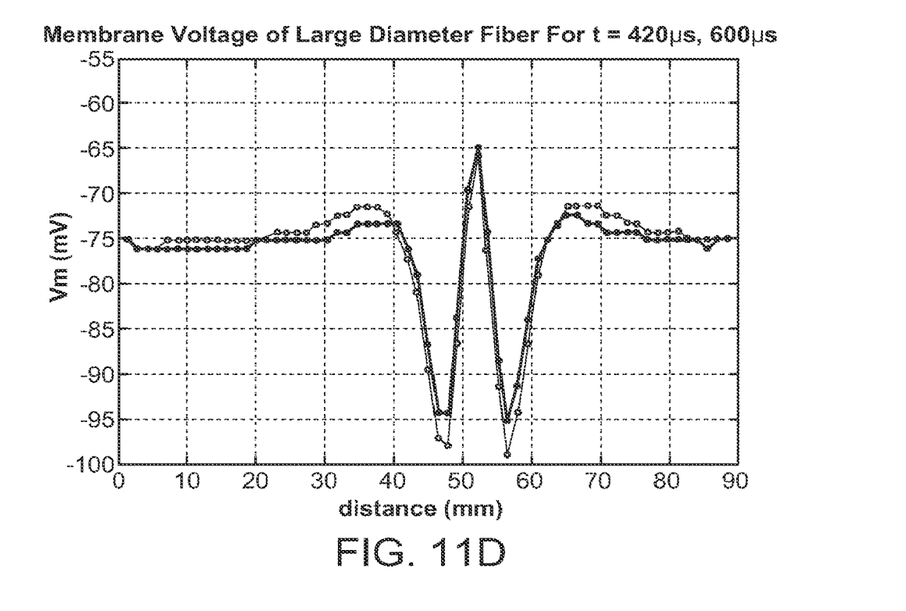
FIG. 11D is a two-dimensional diagram showing membrane voltage of the large diameter fiber of FIG. 11B plotted against distance along fiber for two different times.
Figure 11E:
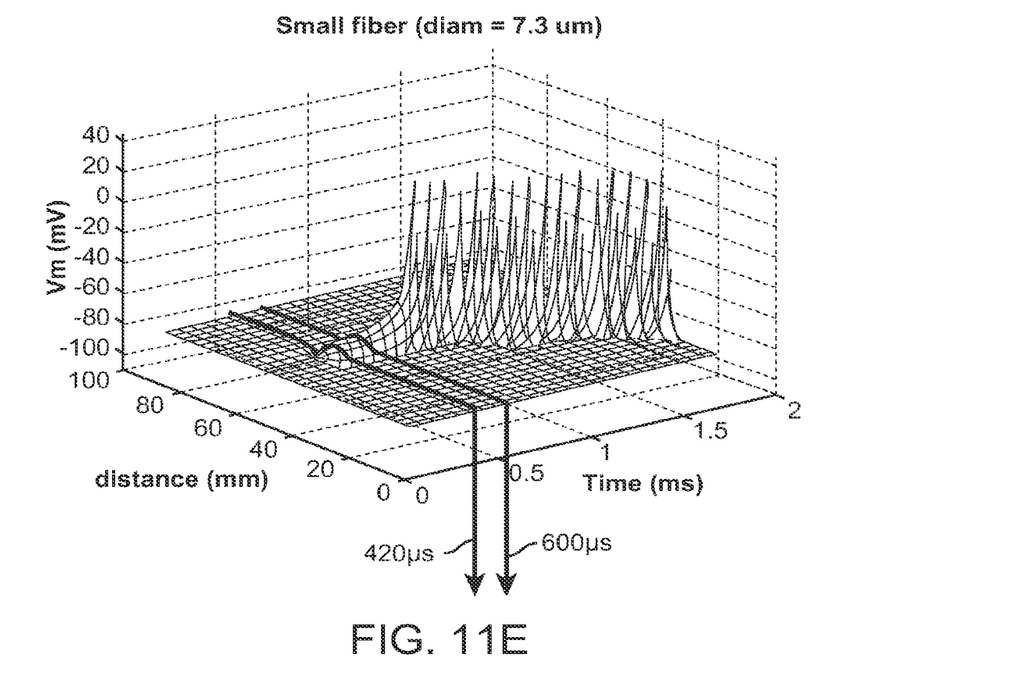
FIG. 11E is a three-dimensional diagram showing membrane voltage of the small diameter fiber of FIG. 11B plotted against time and distance along fiber.
Figure 11F:
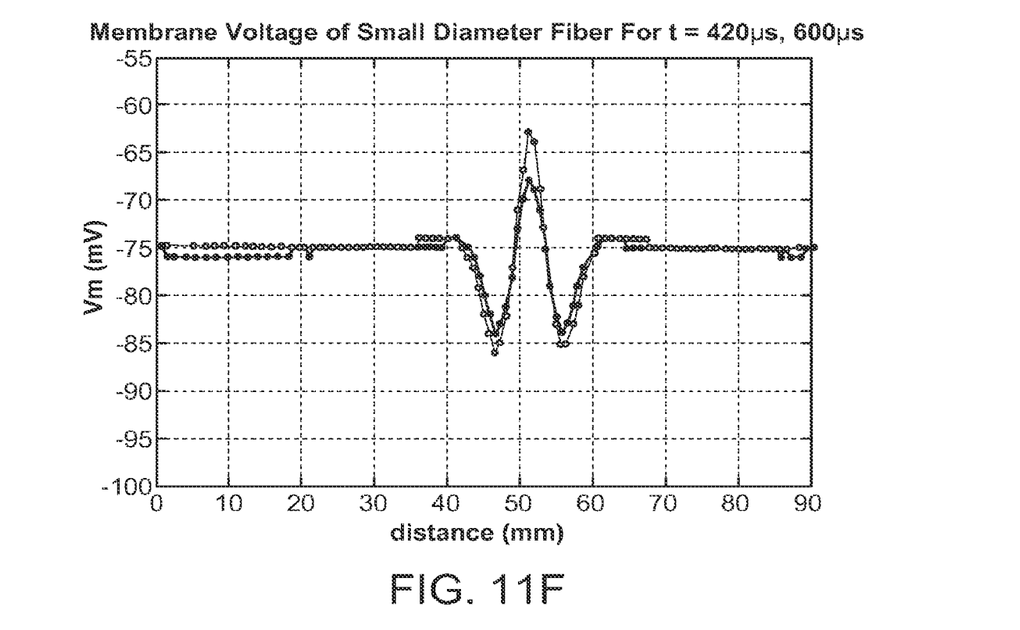
FIG. 11F is a two-dimensional diagram showing membrane voltage of the small diameter fiber of FIG. 11B plotted against distance along fiber for two different times.

The change in membrane voltages during the 1 ms pulse was plotted along the lengths of the respective large- and small-diameter nerve fibers, as shown in FIGS. 11C and 11E. To examine the mechanism of the reversed recruitment order, the membrane voltage potential at two different time points were plotted for the respective large- and small-diameter nerve fibers, as shown in FIGS. 11D and 11F. In each plot, the black line represents the membrane potential during the early phase of the stimulus pulse (at 420 μs), and the grey line represents the membrane voltage 180 μs later (at 600 μs). Each dot represents the location of a node of Ranvier. At the beginning of the pulse (black line with filled circle), the large fiber's central node (closest to the cathode) in FIG. 9D was more depolarized than that of the small fiber's central node in FIG. 9F. However, the depolarized nodes in the large nerve fiber could not generate an action potential, as shown in FIG. 9C, because of the strong surrounding hyperpolarization seen at flanking nodes. In essence, the intensified anodes create very intense internal current "sinks" at the nearby hyperpolarized nodes, such that the membrane potential directly underneath the cathode is pulled down and not allowed to further depolarize. In contrast, in the small nerve fiber, although the depolarization amplitude at the central node was weak in the early phase of the stimulus pulse (black line with filled circle), there are more contiguous depolarized nodes, such that the intense internal current sinks seen around the depolarized nodes in the large fiber are not present. As a result, the membrane voltage potential was able to overcome the hyperpolarization force in the neighboring nodes, and thus increase (grey line with empty circle), to ultimately generate an action potential (shown in FIG. 9E).

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method for delivering a therapy to a patient using a tripolar rostro-caudal arrangement of electrodes positioned local to a spinal cord tissue region targeted for therapy, where the tripolar rostro-caudal arrangement of electrodes includes a local cathode and a two guarding local anodes on opposite sides of the local cathode, the method comprising:
   delivering therapeutic electrical stimulation using the tripolar rostro-caudal arrangement of electrodes to preferentially stimulate relatively small diameter nerve fibers over relatively large diameter nerve fibers, the therapeutic electrical stimulation including local anodic current sourced from the local anodes and local cathodic current sunk into the local cathode, wherein delivering therapeutic electrical stimulation includes reversing an expected nerve fiber recruitment order in which the relatively large diameter nerve fibers would be activated prior to the relatively small diameter nerve fibers, wherein reversing the normal nerve fiber recruitment order includes:
   hyperpolarizing nodes in the large diameter nerve fibers to prevent action potentials in the relatively large diameter nerve fibers, wherein hyperpolarizing nodes in the relatively large diameter nerve fibers includes sourcing the local anodic current from the local anodes in the tripolar rostro-caudal arrangement of electrodes;
   depolarizing both the relatively large diameter nerve fibers and the relatively small diameter nerve fibers by sinking the local cathodic current into the local cathode in the tripolar rostro-caudal arrangement of electrodes, wherein the local cathodic current corresponds to a portion of the local anodic current, and wherein the local anodic current is sufficient to prevent the local cathodic current from generating action potentials in the relatively large diameter nerve fibers and is not sufficient to prevent the local cathodic current from generating action potentials in the small diameter nerve fibers; and
   sinking a remote cathodic current into at least one remote cathode, the remote cathode current corresponding to a remaining portion of the local anodic current.

2. The method of claim 1, wherein the sinking the local cathodic current and the sinking the remote cathodic current occur simultaneously.

3. The method of claim 1, wherein the sinking the local cathodic current and the sinking the remote cathodic current occur at different times.

4. The method of claim 1, wherein a ratio of local anodic current to local cathodic current is at least 1.5.

5. The method of claim 1, wherein a ratio of local anodic current to local cathodic current is at least 1.8.

6. The method of claim 1, wherein a ratio of local anodic current to local cathodic current is at least 2.4.

7. The method of claim 6, wherein each of the local anodes sources anodic current equal to 120% of the local cathodic current.

8. The method of claim 1, wherein the at least one remote cathode includes an electrode disposed on a case of an implantable pulse generator.

9. The method of claim 1, wherein the at least one remote cathode includes an electrode located adjacent another target neural tissue region.

10. The method of claim 1, wherein the local anodic current is equally distributed between the local anodes.

11. The method of claim 1, wherein the local anodic current is unequally distributed between the local anodes.

12. A system for delivering a therapy to a patient having a spinal cord region targeted for the therapy where the spinal cord region includes relatively large diameter nerve fibers and relatively small diameter nerve fibers, and where a normal nerve fiber recruitment order activates the relatively large diameter nerve fibers prior to the relatively small diameter nerve fibers, the system comprising:
    a tripolar rostro-caudal arrangement of electrodes configured to be positioned local to the spinal cord tissue region, the tripolar rostro-caudal arrangement of electrodes including a local cathode and a two guarding local anodes on opposite sides of the local cathode;
    at least one remote cathode;
    a neural stimulator configured use the tripolar rostro-caudal arrangement of electrodes deliver therapeutic electrical stimulation wherein the therapeutic electrical stimulation includes local anodic current sourced from the local anodes and local cathodic current sunk into the local cathode, the neural stimulator being configured to deliver the therapeutic electrical stimulation to preferentially stimulate relatively small diameter nerve fibers over relatively large diameter nerve fibers by reversing an expected nerve fiber recruitment order in which the relatively large diameter nerve fibers would be activated prior to the relatively small diameter nerve fibers, wherein the neural stimulator is configured to:
    source the local anodic current from the local anodes in the tripolar rostro-caudal arrangement of electrodes to hyperpolarize nodes in the large diameter nerve fibers;
    sink a local cathodic current into the local cathode in the tripolar rostro-caudal arrangement of electrodes to depolarize both the relatively large diameter nerve fibers and the relatively small diameter nerve fibers, wherein the local cathodic current corresponds to a portion of the local anodic current, and wherein the local anodic current is sufficient to prevent the local cathodic current from generating action potentials in the relatively large diameter nerve fibers and is not sufficient to prevent the local cathodic current from generating action potentials in the small diameter nerve fibers; and
    sink a remote cathodic current into at least one remote cathode, the remote cathode current corresponding to a remaining portion of the local anodic current.

13. The system of claim 12, wherein the at least one remote cathode includes an electrode disposed on a case of an implantable pulse generator.

14. The system of claim 12, wherein the at least one remote cathode includes an electrode located adjacent another target neural tissue region.

15. The system of claim 12, wherein the local anodic current is equally distributed between the local anodes.

16. The system of claim 12, wherein the sinking the local cathodic current and the sinking the remote cathodic current occur simultaneously.

17. The system of claim 12, wherein the sinking the local cathodic current and the sinking the remote cathodic current occur at different times.

18. The system of claim 12, wherein a ratio of local anodic current to local cathodic current is at least 1.5.

19. A non-transitory machine-readable medium including instructions, which when executed by a machine, cause the machine to deliver a therapy to a patient using a tripolar rostro-caudal arrangement of electrodes positioned local to a spinal cord tissue region targeted for therapy, where the tripolar rostro-caudal arrangement of electrodes includes a local cathode and a two guarding local anodes on opposite sides of the local cathode,
    wherein deliver the therapy includes deliver therapeutic electrical stimulation using the tripolar rostro-caudal arrangement of electrodes to preferentially stimulate relatively small diameter nerve fibers over relatively large diameter nerve fibers, the therapeutic electrical stimulation including local anodic current sourced from the local anodes and local cathodic current sunk into the local cathode, wherein deliver therapeutic electrical stimulation includes reverse an expected nerve fiber recruitment order in which the relatively large diameter nerve fibers would be activated prior to the relatively small diameter nerve fibers,
    wherein reverse the normal nerve fiber recruitment order includes:
    hyperpolarize nodes in the large diameter nerve fibers to prevent action potentials in the relatively large diameter nerve fibers, wherein hyperpolarize nodes in the relatively large diameter nerve fibers includes source the local anodic current from the local anodes in the tripolar rostro-caudal arrangement of electrodes;
    depolarize both the relatively large diameter nerve fibers and the relatively small diameter nerve fibers by sinking the local cathodic current into the local cathode in the tripolar rostro-caudal arrangement of electrodes, wherein the local cathodic current corresponds to a portion of the local anodic current, and wherein the local anodic current is sufficient to prevent the local cathodic current from generating action potentials in the relatively large diameter nerve fibers and is not sufficient to prevent the local cathodic current from generating action potentials in the small diameter nerve fibers; and
    sink a remote cathodic current into at least one remote cathode, the remote cathode current corresponding to a remaining portion of the local anodic current.

20. The non-transitory machine-readable medium of claim 19, wherein the at least one remote cathode includes an electrode disposed on a case of an implantable pulse generator or an electrode located adjacent another target neural tissue region.

* * * * *